(12) United States Patent
Konishi et al.

(10) Patent No.: US 6,506,913 B2
(45) Date of Patent: Jan. 14, 2003

(54) DIMETHYLFURANCARBOXYANILIDE DERIVATIVES

(75) Inventors: Kiyoshi Konishi, Tama (JP); Toshiaki Yanai, Yokohama (JP); Akio Saito, Chiba (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 10/040,138

(22) Filed: Oct. 24, 2001

(65) Prior Publication Data

US 2002/0091154 A1 Jul. 11, 2002

Related U.S. Application Data

(62) Division of application No. 09/729,546, filed on Dec. 4, 2000, now Pat. No. 6,380,247, which is a continuation of application No. 09/306,170, filed on May 6, 1999, now abandoned, which is a division of application No. 08/999,547, filed on Dec. 29, 1997, now Pat. No. 5,977,168, which is a continuation-in-part of application No. 08/730,751, filed on Oct. 15, 1996, now abandoned, which is a continuation of application No. PCT/JP94/00631, filed on Apr. 15, 1994.

(51) Int. Cl.$^7$ ............................................. C07D 307/68
(52) U.S. Cl. ...................................................... 549/487
(58) Field of Search ........................................ 549/487

(56) References Cited

U.S. PATENT DOCUMENTS

| | | | |
|---|---|---|---|
| 3,959,481 A | 5/1976 | Davis et al. | 424/285 |
| 4,117,150 A | 9/1978 | Pommer et al. | 424/285 |
| 5,330,995 A | 7/1994 | Eicken et al. | 514/355 |
| 5,416,103 A | 5/1995 | Eicken et al. | 514/355 |
| 5,480,897 A | 1/1996 | Eicken et al. | 514/355 |
| 5,556,988 A | 9/1996 | Eicken et al. | 514/355 |
| 5,589,493 A | 12/1996 | Eicken et al. | 514/355 |

FOREIGN PATENT DOCUMENTS

| | | |
|---|---|---|
| CA | 2102669 | 5/1994 |
| EP | 0 545 099 A2 | 6/1993 |
| EP | 589313 | 3/1994 |
| EP | 597336 | 5/1994 |
| GB | 1263125 | 2/1972 |
| GB | 1592837 | 7/1981 |
| JP | 5-112406 | 5/1993 |

OTHER PUBLICATIONS

*Chemical Abstracts*, vol. 119, No. 11, Sep. 13, 1993, Abstract No. 111279, Konishi, Seiji et al. of JP 5–112,406.

*Primary Examiner*—Bernard Dentz
(74) *Attorney, Agent, or Firm*—Frishauf, Holtz, Goodman & Chick, P.C.

(57) ABSTRACT

A dimethylfurancarboxyanilide compound of the formula (I):

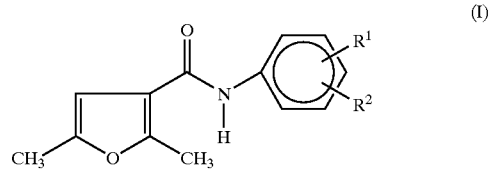

wherein $R^1$ and $R^2$ are the same or different and each is hydrogen, $(C_2-C_6)$-alkyl, $(C_3-C_6)$-cycloalkyl, $(C_3-C_6)$-alkenyl, $(C_2-C_6)$ alkynyl, $(C_1-C_3)$-halogenoalkyl, $(C_2-C_6)$-alkoxy, $(C_1-C_6)$-alkoxy-$(C_1-C_6)$-alkyl, cyano, substituted amide, $(C_1-C_6)$-alkoxy-carbonyl, benzoyl which is unsubstituted or has 1 to 2 substituents, benzoylamino which is unsubstituted or has 1 to 2 substituents; $(C_2-C_6)$-alkanoylamino, $(C_3-C_6)$-cycloalkylcarbonylamino, benzyl which is unsubstituted or has 1 to 2 substituents, phenyl which is unsubstituted or has 1 to 2 substituents, or $(C_1-C_6)$-alkoxycarbonyl-$(C_2-C_5)$-alkenylene; and $R^1$ and $R^2$ do not both represent hydrogen at the same time. A wood preservative containing the dimethylfurancarboxyanilide compound as an active ingredient. A method of preserving wood by applying the dimethylfurancarboxyanilide compound to wood. A wood preservative composition in which the dimethylfurancarboxyanilide compound is combined with at least one of 3-bromo-2,3-diiodo-2-propenylethylcarbamate, 3-iodo-2-propynylbutylcarbamate and 4-chlorophenyl-3-iodopropargylformal.

6 Claims, 4 Drawing Sheets

DIMETHYLFURANCARBOXYANILIDE DERIVATIVES

This is a divisional application of application Ser. No. 09/729,546, filed Dec. 4, 2000 (U.S. Pat. No. 6,380,247), which is a continuation application of application Ser. No. 09/306,170, filed May 6, 1999 (abandoned), which is a divisional application of application Ser. No. 08/999,547 filed Dec. 29, 1997 (U.S. Pat. No. 5,977,168), which is a continuation-in-part application of Ser. No. 08/730,751 filed Oct. 15, 1996 (abandoned), which is a continuation application of International application PCT/JP94/00631 (not published in English), filed Apr. 15, 1994.

BACKGROUND OF THE INVENTION

1. Technological Field

The present invention is concerned with novel dimethylfurancarboxyanilide derivatives exhibiting an excellent antimicrobial effect, a wood preservative containing the dimethylfurancarboxyanilide derivative as the active ingredient, and a wood preservative composition in which the dimethylfurancarboxyanilide derivative as one of the active ingredients is combined with any commercially available wood preservative the effect of which has been already confirmed.

2. Background Technology

Various kinds of inorganic or organic compounds have previously been employed to preserve timber against decay due to various wood-rotting fungi. However, these chemicals have faults such as affecting the human body because of their high toxicity, showing environmental polution, requiring a high concentration thereof when employed and being expensive.

As for compounds relating to the dimethylfurancarboxyanilide derivatives of the present invention, compounds represented by the formula below have been disclosed in Japanese Patent Kokai Application Sho 50-10376 as a chemical for preventing plant injury; in which, however, R is limited to phenyl, nitro-substituted phenyl, carboxy-substituted phenyl, phenyl-substituted phenyl, methyl-substituted phenyl, halogen-substituted phenyl or methoxy-substituted phenyl. In addition, this patent is silent on the other derivatives, and no activity of these compounds on wood-rotting fungi has been described.

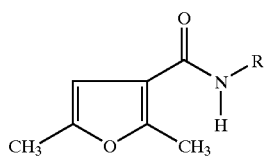

(II)

SUMMARY OF THE INVENTION

The object of the present invention exists in providing a novel wood preservative which is safer, and is possible to use effectively at a low concentration and/or at a low price.

In consideration of such situation as mentioned above, the present inventors considered furancarboxyanilide derivatives, and studied eagerly. Our study resulted in finding that novel dimethylfurancarboxyanilide derivatives represented by the general formula (I) below are very useful as a wood preservative and furthermore, if the dimethylfurancarboxyanilide derivative as the active ingredient is combined with any other commercially available wood preservative, potentiation effect can be observed and a wood preservative composition can be prepared.

The compounds of the present invention are the dimethylfurancarboxyanilide derivatives represented by the general formula

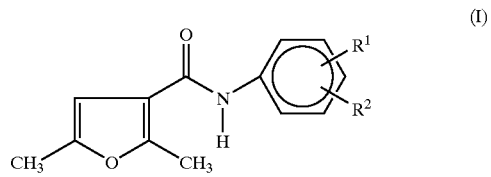

(I)

In this formula, $R^1$ and $R^2$ are the same or different and each represents hydrogen atom; an alkyl group having from 2 to 6 carbon atoms; a cycloalkyl group having from 3 to 6 carbon atoms; an alkenyl group having from 3 to 6 carbon atoms; an alkynyl group having from 2 to 6 carbon atoms; a halogenoalkyl group having from 1 to 3 carbon atoms; an alkoxy group having from 2 to 6 carbon atoms; an alkoxyalkylene group having from 1 to 6 carbon atoms in the alkoxy moiety and having from 1 to 6 carbon atoms in the alkylene moiety; a cyano group; a substituted amide group; an alkoxycarbonyl group having from 1 to 6 carbon atoms in the alkoxy moiety; a benzoyl group which may have optionally from 1 to 2 substituents; a benzoylamino group which may have optionally from 1 to 2 substituents; an alkanoylamino group having from 2 to 6 carbon atoms; a cycloalkylcarbonylamino group having from 3 to 6 carbon atoms in the cycloakyl moiety; a benzyl group which may have optionally from 1 to 2 substituents; a phenyl group which may have optionally from 1 to 2 substituents; or an alkoxycarbonylalkenylene group having from 1 to 6 carbon atoms in the alkoxy moiety and having from 2 to 5 carbon atoms in the alkenylene moiety; and $R^1$ and $R^2$ do not represent hydrogen atoms at the same time]. The present invention concerns the compounds mentioned above, a wood preservative and a wood preservative composition each containing the dimethylfurancarboxyanilide derivative as the active ingredient.

DETAILED DESCRIPTION OF THE INVENTION

Figure 1A:
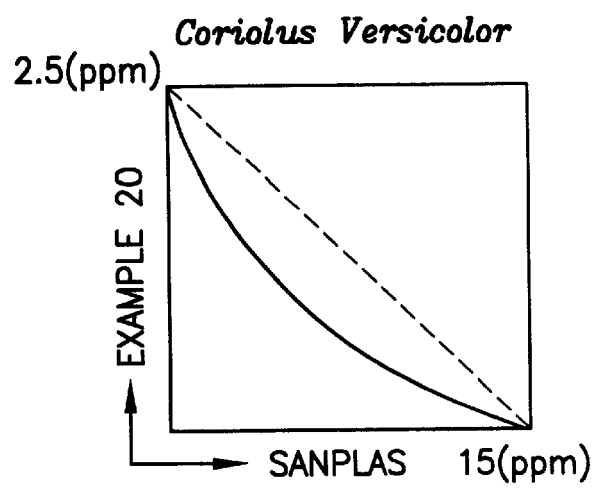
FIGS. 1A to 1F show the minimum inhibitory concentrations (ppm) of Compound of Example 20 in combination with various wood preservatives.

In the general formula (I) above, as an alkyl group having from 2 to 6 carbon atoms, which is included in the definitions for $R^1$ and $R^2$, there may be mentioned a straight or branched chain alkyl group such as ethyl, propyl, isopropyl, butyl, isobutyl, sec-butyl, tert-butyl, pentyl, isopentyl, neopentyl, hexyl, isohexyl or sec-hexyl; particularly preferably an alkyl group having from 2 to 6 carbon atoms.

In the general formula (I) above, as a cycloalkyl group having from 3 to 6 carbon atoms, which is included in the definitions for $R^1$ and $R^2$, there may be mentioned a cycloalkyl group such as cyclopropyl, cyclobutyl, cyclopentyl, or cyclohexyl; preferably a cycloalkyl group having from 3 to 6 carbon atoms; and more preferably a cycloalkyl group having from 5 to 6 carbon atoms.

In the general formula (I) above, as an alkenyl group having from 3 to 6 carbon atoms, which is included in the definitions for $R^1$ and $R^2$, there may be mentioned an alkenyl group such as allyl, isopropenyl, metallyl, 2-butenyl, 3-butenyl, 1,3-butandienyl, 2-pentenyl, or 2-hexenyl; preferably an alkenyl group having from 3 to 4 carbon atoms; and more preferably isopropenyl.

In the general formula (I) above, as an alkynyl group having from 2 to 6 carbon atoms, which is included in the definitions for $R^1$ and $R^2$, there may be mentioned an alkynyl group such as ethynyl, propargyl, 2-butynyl, 4-pentynyl, or 2-hexynyl; preferably an alkynyl group having from 2 to 4 carbon atoms; and more preferably ethynyl.

In the general formula (I) above, as a halogenoalkyl group having from 1 to 3 carbon atoms, which is included in the definitions for $R^1$ and $R^2$, there may be mentioned a halogenoalkyl group such as trifluoromethyl, trichloromethyl, pentafluoroethyl, 2,2,2-trichloroethyl or 2,4-dichloropropyl; preferably a halogenoalkyl group having from 1 to 2 carbon atoms; and more preferably trifluoromethyl.

In the general formula (I) above, as an alkoxy group having from 2 to 6 carbon atoms, which is included in the definitions for $R^1$ and $R^2$, there may be mentioned a straight or branched chain alkoxy group such as ethoxy, propoxy, isopropoxy, butoxy, pentoxy or hexyloxy; preferably an alkoxy group having from 2 to 4 carbon atoms; and more preferably an alkoxy group having from 2 to 3 carbon atoms.

In the general formula (I) above, as an alkoxy group having from 1 to 6 carbon atoms contained in an alkoxyalkyl group having from 1 to 6 carbon atoms in the alkoxy moiety and having from 1 to 6 carbon atoms in the alkyl moiety, which is included in the definitions for $R^1$ and $R^2$, there may be mentioned a straight or branched chain alkoxy group such as methoxy, ethoxy, propoxy, isopropoxy, butoxy, pentoxy, neo-pentoxy or hexyloxy; preferably an alkoxy group having from 1 to 5 carbon atoms; and more preferably an alkoxy group having from 1 to 3 carbon atoms or having 5 carbon atoms.

In the general formula (I) above, as an alkylene group contained in an alkoxyalkylene group having from 1 to 6 carbon atoms in the alkoxy moiety and from 1 to 6 carbon atoms in the alkylene moiety which is included in the definitions for $R^1$ and $R^2$, there may be mentioned a straight or branched chain alkylene group such as methylene, ethylene, propylene, trimethylene, tetramethylene, pentamethylene or hexamethylene; preferably an alkylene group having from 1 to 2 carbon atoms; and more preferably methylene.

In the general formula (I) above, as a substituted amide group, which is included in the definitions for $R^1$ and $R^2$, there may be mentioned a monoalkylamide group such as methylamide, ethylamide, isopropylamide, butylamide, sec-butylamide; a dialkylamide group such as dimethylamide, diethylamide, diisopropylamide, dibutylamide, di-sec-butylamide, methylethylamide, methylisopropylamide, methylbutylamide, methyl-sec-butylamide, ethylisopropylamide, isopropylbutylamide, pyrrolidylamide or piperidylamide; an optionally substituted phenylamide such as phenylamide, 2-chlorophenylamide, 2,4-dichlorophenylamide, 2-methylphenylamide, 2-ethylphenylamide or 4-methoxyphenylamide; preferably methylamide, piperidylamide or phenylamide.

In the general formula (I) above, as an alkoxycarbonyl group having from 1 to 6 carbon atoms in the alkoxy moiety, which is included in the definitions for $R^1$ and $R^2$, there may be mentioned a group which is formed from the aforementioned alkoxy group having from 1 to 6 carbon atoms contained in an alkoxyalkyl group having from 1 to 6 carbon atoms in the alkoxy moiety and having from 1 to 6 carbon atoms in the alkyl moiety and from a carbonyl group, such as methoxycarbonyl, ethoxycarbonyl, isopropoxycarbonyl, butoxycarbonyl, sec-butoxycarbonyl, tert-butoxycarbonyl, pentyloxycarbonyl or hexyloxycarbonyl; preferably an alkoxycarbonyl group having from 1 to 3 carbon atoms in the alkoxy moiety.

In the general formula (I) above, as a benzoyl group which may have optionally from 1 to 2 substituents, which is included in the definitions for $R^1$ and $R^2$, there may be mentioned an optionally substituted benzoyl group such as benzoyl, 2-chlorobenzoyl, 2,4-dichlorobenzoyl, 2-methylbenzoyl, 2,4-dimethylbenzoyl, 4-ethylbenzoyl or 4-methoxybenzoyl; preferably benzoyl.

In the general formula (I) above, as a benzoylamino group which may have optionally from 1 to 2 substituents, which is included in the definitions for $R^1$ and $R^2$, there may be mentioned an optionally substituted benzoylamino group which is formed by substitution of amino group(s) to the aforementioned benzoyl group which may have optionally from 1 to 2 substituents such as benzoylamino, 2-chlorobenzoylamino, 2,4-dichlorobenzoylamino, 2,4-dimethylbenzoylamino, 4-methylbenzoylamino, 4-ethylbenzoylamino or 4-methoxybenzoylamino; preferably benzoylamino.

In the general formula (I) above, as an alkanoylamino group having from 2 to 6 carbon atoms, which is included in the definitions for $R^1$ and $R^2$, there may be mentioned acetylamino, propionylamino, butyrylamino, isobutyrylamino, valerylamino, isovalerylamino, caproylamino or isocaproylamino; preferably acetylamino.

In the general formula (I) above, as a cycloalkylcarbonylamino group having from 3 to 6 carbon atoms in the cycloalkyl moiety, which is included in the definitions for $R^1$ and $R^2$, there may be mentioned cyclopropylcarbonylamino, cyclobutylcarbonylamino, cyclopentylcarbonylamino or cyclohexylcarbonylamino; preferably cyclohexylcarbonylamino.

In the general formula (I) above, as a benzyl group which may have optionally from 1 to 2 substituents, which is included in the definitions for $R^1$ and $R^2$, there may be mentioned benzyl, 2-methylbenzyl, 2,4-dimethylbenzyl, 2-chlorobenzyl, 4-methoxybenzyl or 4-ethoxybenzyl; preferably benzyl.

In the general formula (I) above, as an alkoxycarbonylalkenylene group having from 1 to 6 carbon atoms in the alkoxy moiety and having from 2 to 5 carbon atoms in the alkenylene moiety, which is included in the definitions for $R^1$ and $R^2$, there may be mentioned methoxycarbonylvinylene, ethoxycarbonyl-2-propenylene, methoxycarbonyl-2-butenylene or ethoxycarbonyl-2-pentenylene; preferably methoxycarbonylvinylene.

Preferred compound having the general formula (I) above include ones in which:

(1) $R^1$ and $R^2$ are the same or different and each represents a hydrogen atom; an alkyl group having from 2 to 6 carbon atoms; an alkenyl group having from 3 to 4 carbon atoms; an alkynyl group having from 2 to 4 carbon atoms; a cycloalkyl group having from 3 to 6 carbon atoms; an alkoxycarbonyl group having from 1 to 6 carbon atoms in the alkoxy moiety; an alkoxyalkylene group having from 1 to 6 carbon atoms in the alkoxy moiety and having from 1 to 2 carbon atoms in the alkylene moiety; a cycloalkylcarbonylamino group having from 3 to 6 carbon atoms in the cycloalkyl moiety; an alkoxy group having from 2 to 4 carbon atoms; a benzoyl group which may have optionally from 1 to 2 substituents; a benzyl group which may have optionally from 1 to 2 substituents; or an alkoxycarbonylalkenylene group having from 1 to 6 carbon atoms in the alkoxy moiety and having from 2 to 5 carbon atoms in the alkenylene moiety; and $R^1$ and $R^2$ do not represent hydrogen atoms at the same time. More preferred ones include those in which:

(2) $R^1$ and $R^2$ are the same or different and each represents a hydrogen atom; an alkyl group having from 2 to 6 carbon atoms; an alkenyl group having from 3 to 4 carbon atoms; a cycloalkyl group having from 5 to 6 carbon atoms; an alkoxycarbonyl group having from 1 to 3 carbon atoms in the alkoxy moiety; an alkoxymethylene group having from 1 to 6 carbon atoms in the alkoxy moiety; a cycloalkylcarbonylamino group having from 4 to 6 carbon atoms in the cycloalkyl moiety; a benzoyl group; a benzyl group which may have optionally 1 substituent; or an alkoxycarbonylalkenylene group having from 1 to 3 carbon atoms in the alkoxy moiety and having from 2 to 4 carbon atoms in the alkenylene moiety; and $R^1$ and $R^2$ do not represent hydrogen atoms at the same time. Particularly preferred ones include those in which:

(3) $R^1$ is a 3-alkyl group having from 2 to 6 carbon atoms; a 3-alkoxycarbonyl group having from 1 to 3 carbon atoms in the alkoxy moiety; a 3-alkoxymethylene group having from 1 to 3 carbon atoms in the alkoxy moiety; a cycloalkylcarbonylamino group having from 4 to 6 carbon atoms in the cycloalkyl moiety; a benzoyl group which may be substituted by a methoxy group; a benzoyl group; or an alkoxycarbonylalkenylene group having from 1 to 3 carbon atoms in the alkoxy moiety and having from 2 to 3 carbon atoms in the alkenylene moiety; and (4) $R^2$ is a hydrogen atom.

Novel dimethylfurancarboxyanilide derivatives which may be used as an active ingredient of the wood preservative of the present invention are exemplified in the following table.

| | |
|---|---|
| Bz | Benzyl |
| Bu | Butyl |
| Et | Ethyl |
| Hx | Hexyl |
| Me | Methyl |
| Ph | Phenyl |
| Pip | Piperidyl |
| Pn | Pentyl |
| Pr | Propyl |
| i | iso |
| s | secondary |
| t | tertiary |
| c | cyclo |

TABLE 1

| Compound No. | $R^1$ | $R^2$ |
|---|---|---|
| 1 | 3-CF$_3$ | H |
| 2 | 4-CF$_3$ | H |
| 3 | 3-CH$_2$OMe | H |
| 4 | 4-CH$_2$OMe | H |
| 5 | 2-Et | H |
| 6 | 3-Et | H |
| 7 | 4-Et | H |
| 8 | 3-C≡CH | H |
| 9 | 4-C≡CH | H |

TABLE 1-continued

| Compound No. | $R^1$ | $R^2$ |
|---|---|---|
| 10 | 3-CH$_2$OEt | H |
| 11 | 4-CH$_2$OEt | H |
| 12 | 2-Et | 3-Et |
| 13 | 2-Et | 4-Et |
| 14 | 2-Et | 5-Et |
| 15 | 2-Et | 6-Et |
| 16 | 3-Et | 4-Et |
| 17 | 3-Et | 5-Et |
| 18 | 3-Et | 6-Et |
| 19 | 3-Pr | H |
| 20 | 4-Pr | H |
| 21 | 2-iPr | H |
| 22 | 3-iPr | H |
| 23 | 4-iPr | H |
| 24 | 3-cPr | H |
| 25 | 4-cPr | H |
| 26 | 3-CH$_2$OPr | H |
| 27 | 3-CH$_2$OiPr | H |
| 28 | 4-CH$_2$OiPr | H |
| 29 | 3-CH$_2$C=CH$_2$ | H |
| 30 | 4-CH$_2$C=CH$_2$ | H |
| 31 | 3-CH$_2$C≡CH | H |
| 32 | 4-CH$_2$C≡CH | H |
| 33 | 3-Pr | 4-Pr |
| 34 | 2-iPr | 4-iPr |
| 35 | 3-iPr | 5-iPr |
| 36 | 3-CH$_2$OBu | H |
| 37 | 4-CH$_2$OBu | H |
| 38 | 3-CH$_2$OiBu | H |
| 39 | 4-CH$_2$OiBu | H |
| 40 | 3-CH$_2$OsBu | H |
| 41 | 4-CH$_2$OsBu | H |
| 42 | 3-Bu | H |
| 43 | 4-Bu | H |
| 44 | 3-iBu | H |
| 45 | 3-sBu | H |
| 46 | 3-cBu | H |
| 47 | 4-cBu | H |
| 48 | 3-tBu | H |
| 49 | 3-CH$_2$CH=CHMe | H |
| 50 | 3-CH$_2$C≡CMe | H |
| 51 | 3-CH$_2$MeCH=CH$_2$ | H |
| 52 | 4-CH$_2$MeCH=CH$_2$ | H |
| 53 | 3-Pn | H |
| 54 | 4-Pn | H |
| 55 | 3-iPn | H |
| 56 | 3-cPn | H |
| 57 | 3-neoPn | H |
| 58 | 3-CH$_2$OPn | H |
| 59 | 3-CH$_2$Oneo-Pn | H |
| 60 | 3-Hx | H |
| 61 | 3-iHx | H |
| 62 | 3-cHx | H |
| 63 | 3-CN | H |
| 64 | 3-OEt | H |
| 65 | 3-OiPr | H |
| 66 | 3-CONHMe | H |
| 67 | 3-(co-1-Pip) | H |
| 68 | 3-CONHPh | H |
| 69 | 3-COOMe | H |
| 70 | 3-COOEt | H |
| 71 | 3-COOPr | H |
| 72 | 3-COOiPr | H |
| 73 | 3-COOBu | H |
| 74 | 3-COOtBu | H |
| 75 | 3-COPh | H |
| 76 | 3-CO(2-MePh) | H |
| 77 | 3-NHCOPh | H |
| 78 | 3-NHCOMe | H |
| 79 | 3-NHCOBu | H |
| 80 | 3-NHCOcPn | H |
| 81 | 3-NHCOcHx | H |
| 82 | 3-Bz | H |
| 83 | 3-(4-MeOBz) | H |
| 84 | 3-(4-MeBz) | H |

TABLE 1-continued

| Compound No. | R¹ | R² |
|---|---|---|
| 85 | 3-CH=CHCOOMe | H |
| 86 | 3-Ph | H |
| 87 | 3-(2-MePh) | H |

Among the compounds above, preferred ones include Compound Nos. 3, 4, 5, 6, 7, 8, 10, 11, 15, 16, 17, 18, 19, 20, 21, 22, 23, 24, 25, 26, 27, 28, 29, 31, 33, 35, 36, 38, 40, 42, 43, 44, 45, 46, 48, 49, 50, 51, 53, 54, 55, 56, 57, 58, 59, 60, 61, 62, 64, 69, 70, 71, 72, 75, 80, 81, 82, 83 and 85; and more preferred ones include Compound Nos. 3, 6, 10, 19, 22, 24, 26, 27, 33, 35, 36, 38, 40, 42, 44, 45, 46, 48, 53, 55, 60, 61, 69, 70, 81, 83 and 85.

The compounds of the said general formula (I) may be prepared according to the procedure summarized in either the following Method A or Method B.

Method A

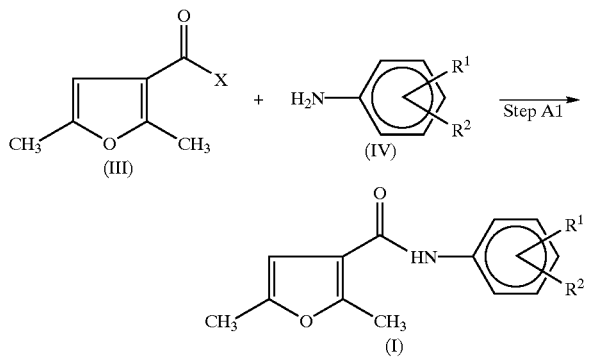

Method B

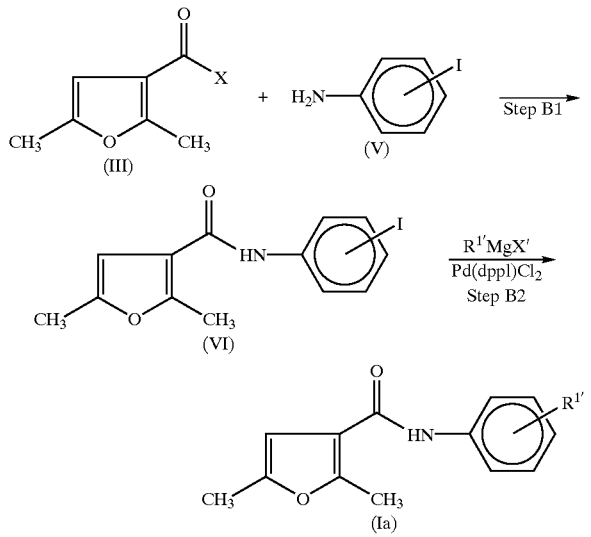

In the above formulae, $R^1$ and $R^2$ are as defined above. $R^{1'}$ represents a $C_1$–$C_6$ alkyl, $C_3$–$C_6$ cycloalkyl or benzyl group which may optionally have 1 or 2 substituents. The compound of formula (Ia) is that of a general formula (I), in which $R^1$ is $R^{1'}$ and $R^2$ signifies a hydrogen atom. The compound of formula (V) is iodine-substituted aniline. X signifies a halogen atom such as chlorine, bromine or iodine, preferably chlorine. X' signifies a halogen atom such as a chlorine, bromine or iodine, preferably bromine or iodine.

The compounds of the present invention may be prepared by well-known procedure.

Step A1 consists of the preparation of a compound of general formula (I) by reacting a compound of general formula (III) with a compound of general formula (IV) in an inert solvent in the presence of a dehydrohalogenating agent.

A compound of formula (III) used as a starting material in this step may be prepared by hydrolyzing 2,5-dimethylfuran-3-carboxylate, which may be prepared by condensing chloroacetone with acetoacetate, followed by halogenation.

A compound of formula (IV) used as a starting material in this step is an aniline derivative which is commercially available or may be prepared by well-known methods.

Examples of the inert solvents used include, for example, ethers such as ether, isopropyl ether, tetrahydrofuran or dioxane; aromatic hydrocarbons such as benzene, toluene or xylene; halogenated hydrocarbons such as dichloromethane, chloroform or carbon tetrachloride; and mixtures of two or more of these solvents; preferably aromatic hydrocarbons (particularly toluene).

Examples of dehydrohalogenating agents used include, for example, tertiary amines such as triethylamine, N,N-dimethylaminopyridine or the like and pyridines. This reaction can be carried out in the presence or absence of a solvent. In order to perform the reaction smoothly, using a solvent, the reaction is carried out at a temperature of 0° C. to reflux temperature of the solvent used, preferably from room temperature to 100° C. The time required for the reaction takes generally from 30 minutes to 5 hours, preferably from 30 minutes to 2 hours.

Step B1 consists of the preparation of a compound having general formula (VI) by reacting a compound having general formula (III) with a compound having general formula (V) in an inert solvent in the presence of a dehydrohalogenating agent.

A compound of formula (IV) used as a starting material in this step is an aniline derivative which is commercially available or may be prepared by well-known methods.

The reaction conditions employed in this step are similar to those employed in Step A1.

Step B2 consists of the preparation of a compound having general formula (Ia) by reacting a compound having general formula (VI) with a Grignard reagent having general formula: $R^{1'}MgX'$ in an inert solvent in the presence of a catalyst.

Examples of preferred inert solvents used include, for example, ethers such as diethyl ether, isopropyl ether, tetrahydrofuran or dioxane; particularly preferably diethyl ether.

As a particularly preferred catalyst there may be used [1,1'-bis(diphenylphosphino)ferrocene]palladium(II) chloride.

The Grignard reagents used in this process are commercially available or can be prepared by reacting magnesium with an alkyl halide represented by formula: $R^{1'}X'$ (wherein $R^{1'}$ and X' are as defined above) according to well-known methods.

The reaction is normally carried out at a temperature of 0° C. to 50° C., preferably at room temperature. Although the time required for the reaction varies depending upon the nature of the solvent and reagent to be used, the reaction is normally complete within a period of 10 hours to 10 days.

The compounds having the said general formula (I) in according with the invention have potent wood preservative activity at low concentration, compared with the activity shown by existing wood preservatives. A composition consisting of a combination of the foregoing compound (I) with a known wood preservative gives a synergistic effect, lower concentrations of each compound being required than would be expected from the activity shown by each singly, such that the composition shows efficient wood preservative activity at a low concentration. Therefore, novel dimethylfurancarboxyanilide derivatives are extremely effective as a wood preservative in low concentration so as to solve one of the problems in the quality of life.

The following Examples illustrate the preparation and the formulation of the compound of the invention in more detail. Such examples are not to be construed as being limitative of the scope of the invention.

EXAMPLE 1

2,5-Dimethylfuran-3-carboxy(3-acetylaminoanilide)

To a solution of 0.50 g of 2,5-dimethylfuran-3-carbonyl chloride in 10 ml of dichloromethane were added 0.44 ml of triethylamine and 0.47 g of 3-acetylaminoaniline under ice-cooling, and the resulting mixture was stirred at room temperature for 2.5 hours followed by heating under reflux for 4.5 hours. After the reaction mixture was cooled, it was diluted by adding 10 ml of dichloromethane. The diluted mixture was successively washed with 1 N sodium hydroxide, 1 N hydrochloric acid and a saturated aqueous solution of sodium chloride and dried over sodium sulfate followed by distilling off the solvent. The residue was purified by column chromatography through silica gel and the desired fractions were recrystallized from ethyl acetate to give 0.51 g of the desired compound as white crystals in a 59.4% yield.

m.p.:172.0–172.5° C.

$^1$H NMR (CDCl$_3$+DMSO) δ ppm: 8.4 (1H, b), 7.95 (1H, b), 7.88 (1H, m), 7.4 (1H, m), 7.32 (1H, m), 7.25 (1H, t, J=8 Hz), 6.25 (1H, s), 2.55 (3H, s), 2.25 (3H, s), 2.15 (3H, s)

IR (KBr) cm$^{-1}$:3306, 1672, 1651, 1086, 781

Elemental analysis (%): Calc'd for $C_{15}H_{16}N_2O_3$: C, 66.16; H, 5.92; N, 10.29. Found: C, 66.30; H, 5.98; N, 10.32.

Following the similar procedure as above, but using an appropriate aniline derivative instead of 3-acetylaminoaniline, there were obtained the following compounds.

EXAMPLE 2

2.5-Dimethylfuran-3-carboxy[3-(N-methylcarbamoyl)anilide]

Yield:42.0% m.p.:212.0–213.0° C.

$^1$H NMR (CDCl$_3$+DMSO) δ ppm: 8.5 (1H, b), 8.05 (1H, m), 7.88 (1H, m), 7.52 (1H, m), 7.38 (1H, t, J=8 Hz), 6.8 (1H, b), 6.35 (1H, s), 2.95 (3H, d, J=1.4 Hz), 2.55 (3H, s), 2.25 (3H, s).

IR (KBr) cm$^{-1}$:3293, 1638, 1581, 1074, 689

Elemental analysis (%): Calc'd for $C_{15}H_{16}N_2O_3$: C, 66.16; H, 5.92; N, 10.29. Found: C, 66.08; H, 6.20; N, 10.28.

EXAMPLE 3

2,5-Dimethylfuran-3-carboxy[3-(1-piperidylcarbonyl)anilide]

Yield:50.0% m.p.:183.0–185.0° C.

$^1$H NMR spectrum (CDCl$_3$) δ ppm: 7.68 (1H, m), 7.55 (2H, m), 7.35 (1H, t, J=8 Hz), 7.1 (1H, m), 6.15 (1H, s), 3.7 (2H, b), 3.35 (2H, b), 2.55 (3H, s), 2.25 (3H, s), 2.75–1.4 (6H, m)

IR (KBr) cm$^{-1}$:3302, 1663, 1615, 1065, 808

Elemental analysis (%): Calc'd for $C_{19}H_{22}N_2O_3$: C, 69.92; H, 6.79; N, 8.58. Found: C, 69.52; H, 6.88; N, 8.48.

EXAMPLE 4

2.5-Dimethylfuran-3-carboxyl[3-(N-phenylcarbamoyl)anilide]

Yield:53.5% m.p.:182.5–184.0° C.

$^1$H NMR (CDCl$_3$+DMSO) δ ppm: 8.48 (1H, b), 8.2 (1H, b), 8.1 (1H, s), 7.95 (1H, m), 7.7 (2H, d, J=8 Hz), 7.65 (1H, d, J=8 Hz), 7.45 (1H, t, J=8 Hz), 7.35 (2H, t, J=8 Hz), 7.15 (1H, t, J=8 Hz), 6.28 (1H, s), 2.55 (3H, s), 2.25 (3H, s)

IR (KBr) cm$^{-1}$:3282, 1646, 1080, 755, 691

Elemental analysis (%): Calc'd for $C_{20}H_{18}N_2O_3$: C, 71.84; H, 5.43; N, 8.38. Found: C, 71.87; H, 5.64; N, 8.34.

EXAMPLE 5

2,5-Dimethylfuran-3-carboxy(3-tert-butoxycarbonylanilide)

Yield:92.0% m.p.:117.0–118.0° C.

$^1$H NMR (CDCl$_3$) δ ppm: 8.05 (1H, m), 7.88 (1H, m), 7.75 (1H, m), 7.4 (1H, t, J=8 Hz), 7.35 (1H, b), 6.1 (1H, s), 2.55 (3H, s), 2.25 (3H, s), 1.65 (9H, s)

IR (KBr) cm$^{-1}$:3362, 1687, 1672, 1067, 757

Elemental analysis (%): Calc'd for $C_{18}H_{21}NO_4$: C, 68.55; H, 6.71; N, 4.44. Found: C, 68.04; H, 7.00; N, 4.40.

EXAMPLE 6

2,5-Dimethylfuran-3-carboxy(3-methoxycarbonylanilide)

Yield:77.1% m.p.:104.0–106.0° C.

$^1$H NMR (CDCl$_3$) δ ppm: 8.05 (1H, m), 7.98 (1H, m), 7.8 (1H, m), 7.42 (1H, t, J=8 Hz), 7.38 (1H, b), 6.1 (1H, s), 3.92 (3H, s), 2.55 (3H, s), 2.25 (3H, s)

IR (KBr) cm$^{-1}$:3437, 1704, 1675, 1070, 759

Elemental analysis (%): Calc'd for $C_{15}H_{15}NO_4$: C, 65.92; H, 5.53; N, 5.13. Found: C, 66.02; H, 5.60; N, 5.08.

EXAMPLE 7

2,5-Dimethylfuran-3-carboxy(3-benzoylanilide)

Yield:69.1% m.p.:137.0–139.0° C.

$^1$H NMR (CDCl$_3$) δ ppm: 8.05 (1H, m), 7.85–7.7 (3H, m), 7.6 (1H, m), 7.55–7.35 (5H, m), 6.1 (1H, s), 2.55 (3H, s), 2.25 (3H, s)

IR (KBr) cm$^{-1}$:3386, 1672, 1647, 1069, 707

Elemental analysis (%): Calc'd for $C_{20}H_{17}NO_3$: C, 75.22; H, 5.37; N, 4.39. Found: C, 75.38; H, 5.43; N, 4.38.

EXAMPLE 8

2,5-Dimethylfuran-3-carboxy(3-benzoylaminoanilide)

Yield: 46.0% m.p.: 194.5–195.0° C.

$^1$H NMR (CDCl$_3$+DMSO) δ ppm: 8.7 (1H, b), 8.1 (1H, m), 7.95 (1H, b), 7.9 (2H, m), 7.6–7.4 (5H, m), 7.3 (1H, t, J=8 Hz), 6.25 (1H, s), 2.55 (3H, s), 2.25 (3H, s)

IR (KBr) cm$^{-1}$ 3283, 1642, 1074, 791, 705

Elemental analysis (%): Calc'd for C$_{20}$H$_{18}$N$_1$O$_3$: C, 71.84; H, 5.43; N, 8.38. Found: C, 71.96; H, 5.53; N, 8.28.

EXAMPLE 9

2,5-Dimethylfuran-3-carboxy(3-valerylaminoanilide)

Yield: 70.3% m.p.: 104.0–105.0° C.

$^1$H NMR (CDCl$_3$) δ ppm: 7.9 (1H, b), 7.45–7.1 (5H, m), 6.1 (1H, s), 2.55 (3H, s), 2.35 (2H, t, J=7 Hz), 2.25 (3H, s), 1.7 (2H, m), 1.4 (2H, m), 0.95 (1H, t, J=7 Hz)

IR (KBr) cm$^{-1}$: 3250, 1660, 1644, 1074, 781

Elemental analysis (%): Calc'd for C$_{18}$H$_{22}$N$_2$O$_3$: C, 68.77; H, 7.05; N, 8.91. Found: C, 68.73; H, 7.17; N, 8.90.

EXAMPLE 10

2,5-Dimethylfuran-3-carboxy(3-cyclohexylcarbonylaminoanilide)

Yield: 45.1% m.p.: 212.5–213.0° C.

$^1$H NMR (CDCl$_3$) δ ppm: 7.92 (1H, b), 7.88 (1H, b), 7.45–7.35 (2H, m), 7.25 (1H, t, J=8 Hz), 6.22 (1H, s), 2.55 (3H, s), 2.25 (3H, s), 2.25–2.2 (1H, m), 2.0–1.2 (10H, m)

IR (KBr) cm$^{-1}$: 3238, 1651, 1639, 1076, 781

Elemental analysis (%): Calc'd for C$_{20}$H$_{24}$N$_2$O$_3$: C, 70.57; H, 7.11; N, 8.23. Found: C, 70.56; H, 7.26; N, 8.16

EXAMPLE 11

2,5-Dimethylfuran-3-carboxy(3-methoxymethylanilide)

Yield: 73.3% m.p.: 102.5–103.5° C.

$^1$H NMR (CDCl$_3$) δ ppm: 7.55 (1H, m), 7.52 (1H, d, J=8 Hz), 7.32 (1H, t, J=8 Hz), 7.32 (1H, b), 6.9 (1H, d, J=8 Hz), 6.1 (1H, s), 4.45 (2H, s), 3.4 (3H, s), 2.55 (3H, s), 2.25 (3H, s)

IR (KBr) cm$^{-1}$: 3278, 1645, 1237, 1107, 784

Elemental analysis (%): Calc'd for C$_{15}$H$_{17}$NO$_3$: C, 69.48; H, 6.61; N, 5.40. Found: C, 69.22; H, 7.02; N, 5.37.

EXAMPLE 12

2,5-Dimethylfuran-3-carboxy(3-ethoxymethylanilide)

Yield: 64.4% m.p.: 85.0–85.5° C.

$^1$H NMR (CDCl$_3$) δ ppm: 7.65–7.55 (2H, m), 7.38 (1H, t, J=8 Hz), 7.35 (1H, b), 7.15 (1H, d, J=8 Hz), 6.15 (1H, s), 4.55 (2H, s), 3.58 (2H, q, J=8 Hz), 2.55 (3H, s), 2.25 (3H, s), 1.3 (3H, t, J=8 Hz)

IR (KBr) cm$^{-1}$: 3279, 1646, 1115, 785

Elemental analysis (%): Calc'd for C$_{16}$H$_{19}$NO$_3$: C, 70.31; H, 7.01; N, 5.12. Found: C, 70.14; H, 7.27; N, 5.06.

EXAMPLE 13

2,5-Dimethylfuran-3-carboxy(3-isopropyloxymethylanilide)

Yield: 92.7% m.p.: 68.0–69.5° C.

$^1$H NMR (CDCl$_3$) δ ppm: 7.55 (1H, d, J=8 Hz), 7.5 (1H, m), 7.3 (1H, t, J=8 Hz), 7.3 (1H, b), 7.12 (1H, d, J=8 Hz), 6.1 (1H, s), 4.5 (2H, s), 3.7 (1H, m), 2.55 (3H, s), 2.25 (3H, s), 1.25 (6H, d, J=7 Hz)

IR (Liquid film) cm$^{-1}$: 3321, 1651, 1072, 785

Elemental analysis (%): Calc'd for C$_{17}$H$_{21}$NO$_3$: C, 71.06; H, 7.37; N, 4.87. Found: C, 70.35; H, 7.14; N, 4.91.

EXAMPLE 14

2,5-Dimethylfuran-3-carboxy[3-(4-methoxybenzyl)anilide]

Yield: 86.8% m.p.: 100.0–102.5° C.

$^1$H NMR (CDCl$_3$) δ ppm: 7.45 (1H, m), 7.35 (1H, m), 7.25 (1H, t, J=8 Hz), 7.25 (2H, b), 7.1 (2H, d, J=8 Hz), 6.92 (1H, d, J=8 Hz), 6.88–6.75 (1H, m), 6.82 (2H, d, J=8 Hz), 6.05 (1H, s), 3.9 (2H, s), 3.75 (3H, s), 2.55 (3H, s), 2.25 (3H, s)

IR (KBr) cm$^{-1}$: 3345, 1656, 1246, 1074, 694

Elemental analysis (%): Calc'd for C$_{21}$H$_{21}$NO$_3$: C, 75.20; H, 6.31; N, 4.18. Found: C, 75.28; H, 6.32; N, 4.21.

EXAMPLE 15

2,5-Dimethylfuran-3-carboxy[3-(2-methoxycarbonylvinyl)anilide]

Yield: 63.3% m.p.: 159.5–161.5° C.

$^1$H NMR (CDCl$_3$) δ ppm: 7.82 (1H, m), 7.7 (1H, d, J=15 Hz), 7.58 (1H, m), 7.38 (1H, b), 7.35 (1H, t, J=8 Hz), 7.28 (1H, m), 6.48 (1H, d, J=15 Hz), 6.12 (1H, s), 3.82 (3H, s), 2.55 (3H, s), 2.25 (3H, s)

IR (KBr) cm$^{-1}$: 3387, 1685, 1670, 1068, 800

Elemental analysis (%): Calc'd for C$_{17}$H$_{17}$NO$_4$: C, 68.22; H, 5.72; N, 4.68. Found: C, 67.55; H, 5.64; N, 4.62.

EXAMPLE 16

2,5-Dimethylfuran-3-carboxy(3-phenylanilide)

Yield: 50.0% m.p.: 90.0–92.0° C.

$^1$H NMR (CDCl$_3$) δ ppm: 7.82 (1H, s), 7.6 (2H, d, J=8 Hz), 7.55 (1H, d, J=8 Hz), 6.48–6.3 (6H, m), 6.12 (1H, s), 2.55 (3H, s), 2.25 (3H, s)

IR (KBr) cm$^{-1}$: 3367, 1646, 1074, 755

Elemental analysis (%): Calc'd for C$_{19}$H$_{17}$NO$_2$: C, 78.33; H, 5.88; N, 4.81. Found: C, 78.17; H, 6.00; N, 4.72.

EXAMPLE 17

2,5-Dimethylfuran-3-carboxy(3-neopentyloxymethylanilide)

Yield: 50.0% m.p.: 95.5–97.0° C.

¹H NMR (CDCl₃) δ ppm: 7.48 (2H, m), 7.32 (1H, t, J=8 Hz), 7.3 (1H, b), 7.12 (1H, d, J=8 Hz), 4.52 (2H, s), 3.12 (2H, s), 2.55 (3H, s), 2.25 (3H, s), 0.95 (9H, s)

IR (KBr) cm⁻¹:3324, 1646, 1091, 700

Elemental analysis (%): Calc'd for $C_{19}H_{25}NO_3$: C, 72.35; H, 7.99; N, 4.44. Found: C, 72.38; H, 8.03; N, 4.20.

EXAMPLE 18

2,5-Dimethylfuran-3-carboxy(3-isopropenylanilide)

Yield:50.0% m.p.:71.0–72.0° C.

¹H NMR (CDCl₃) δ ppm: 7.65 (1H, m), 7.5 (1H, m), 7.3 (1H, b), 7.3 (1H, t, J=8 Hz), 7.22 (1H, m), 6.12 (1H, s), 5.4 (1H, s), 5.1 (1H, s), 2.6 (3H, s), 2.55 (3H, s), 2.25 (3H, s)

IR (KBr) cm⁻¹:3275, 1641, 1580, 1078, 790

Elemental analysis (%): Calc'd for $C_{16}H_{17}NO_2$: C, 75.27; H, 6.71; N, 5.49. Found: C, 75.29; H, 6.88; N, 5.48.

EXAMPLE 19

2,5-Dimethylfuran-3-carboxy(3-ethynylanilide)

Yield:50.0% m.p.:83.0–84.0° C.

¹H NMR (CDCl₃) δ ppm: 7.7 (1H, m), 7.6 (1H, m), 7.32–7.2 (3H, m), 6.1 (1H, s), 3.05 (1H, s), 2.55 (3H, s), 2.25 (3H, s)

IR (KBr) cm⁻¹:3245, 1644, 1079, 796

Elemental analysis (%): Calc'd for $C_{15}H_{13}NO_2$: C, 75.30; H, 5.48; N, 5.85. Found: C, 75.50; H, 5.46; N, 5.96.

EXAMPLE 20

2,5-Dimethylfuran-3-carboxy(3-ethylanilide)

Yield:91.0% m.p.:113–115° C.

Mass (m/z):243 (M⁺), 123.94

¹H NMR (CDCl₃) δ ppm: 7.47–6.95 (4H, m), 6.1 (1H, s), 2.66 (3H, q), 2.60 (3H, s), 2.29 (3H, s), 1.25 (3H, t)

EXAMPLE 21

2,5-Dimethylfuran-3-carboxy(3-isopropylanilide)

Yield:84.0% m.p.:79–80° C.

Mass (m/z):257 (M⁺), 149.135

¹H NMR (CDCl₃) δ ppm: 7.47–6.98 (4H, m), 6.11 (1H, s), 2.91 (1H, q,q), 2.60 (3H, s), 2.29 (3H, s), 1.26 (d, 6H)

EXAMPLE 22

2,5-Dimethylfuran-3-carboxy(2,6-diethylanilide)

Yield:85.2% m.p.:128.0–131.0° C.

Mass (m/z):271 (M⁺), 242.228

¹H NMR (CDCl₃) δ ppm: 7.28–7.12 (3H, m), 6.82 (1H, b), 6.16 (1H, s), 2.63 (4H, q), 2.58 (3H, s), 2.31 (3H, s), 1.20 (6H, t)

EXAMPLE 23

2,5-Dimethylfuran-3-carboxy(3-hexylanilide)

(Step 1) To a solution of 3.95 g of 2,5-dimethylfuran-3-carbonyl chloride in 60 ml of dichloromethane were added 3.45 ml of triethylamine and 2.99 ml of m-iodoaniline under ice-cooling, and the resulting mixture was stirred at room temperature for 6.5 hours. After the reaction mixture was cooled, it was diluted by adding 50 ml of dichloromethane. The diluted mixture was successively washed with 1 N sodium hydroxide, 1 N hydrochloric acid and a saturated aqueous solution of sodium chloride and dried over sodium sulfate followed by distilling off the solvent. The residue was subjected to column chromatography through silica gel to give 7.64 g of 2,5-dimethylfuran-3-carboxy(3-iodoanilide) as pale-yellow crystals in a 89.9% yield.

(Step 2) To a solution of 0.68 g of the crystals obtained in Step 1 in 8 ml of diethyl ether were added 29.3 mg of [1,1'-bis(diphenylphosphino)ferrocene]palladium(II) chloride and 11 ml of 1 M hexylmagnesium bromide, prepared from hexyl bromide and magnesium, divided into six equal parts, and the resulting mixture was stirred at room temperature for 47 hours. After adding 2 N hydrochloric acid to the reaction mixture, the catalyst was filtered off and the filtrate was extracted with diethyl ether. The extract was successively washed with an aqueous solution of sodium bicarbonate and a saturated aqueous solution of sodium chloride and dried over sodium sulfate. After distilling off the solvent, the residue was purified by chromatography through silica gel and then D-ODS-5, YMC-packed column to give 316 mg of the desired compound as white crystals in a 52.8% yield.

m.p.:71.5–72.0° C.

¹H NMR (CDCl₃) δ ppm: 7.45 (1H, m), 7.35 (1H, m), 7.25 (1H, b), 7.22 (1H, t, J=8 Hz), 6.95(1H, d, J=8 Hz), 6.1 (1H, s), 2.65–2.5 (2H, m), 2.55 (3H, s), 2.25 (3H, s), 1.7–1.5 (2H, m), 1.4–1.2 (6H, m), 0.85 (3H, t, J=7 Hz)

IR (KBr) cm⁻¹:3310, 1643, 1077, 788

Elemental analysis (%): Calc'd for $C_{19}H_{25}NO_2$: C, 76.22; H, 8.42; N, 4.68. Found: C, 76.15; H, 8.54; N, 4.55

Following the similar procedure as above, but using an appropriate Grignard reagent instead of hexylmagnesium bromide, there were obtained the following compounds.

EXAMPLE 24

2,5-Dimethylfuran-3-carboxy(3-butylanilide)

Yield:36.4% m.p.:77.0–80.0° C.

¹H NMR (CDCl₃) δ ppm: 7.45 (1H, m), 7.35 (1H, m), 7.25 (1H, b), 7.22 (1H, t, J=8 Hz), 6.95 (1H, d, J=8 Hz), 6.1 (1H, s), 2.65–2.55 (2H, m), 2.55 (3H, s), 2.25 (3H, s), 1.6 (2H, m), 1.35 (2H, m), 0.92 (1H, t, J=7 Hz)

IR (KBR) cm⁻¹:3285, 1646, 1075, 702

Elemental analysis (%): Calc'd for $C_{17}H_{21}NO_2$: C, 75.25; H, 7.80; N, 5.16. Found: C, 75.13; H, 7.87; N, 5.13

EXAMPLE 25

2,5-Dimethylfuran-3-carboxy(3-sec-butylanilide)

Yield:38.1% m.p.:80.0–81.0° C.

¹H NMR (CDCl₃) δ ppm: 7.4 (1H, m), 7.38 (1H, m), 7.25 (1H, b), 7.22 (1H, t, J=8 Hz), 6.95 (1H, d, J=8 Hz), 6.1 (1H, s), 2.65–2.5 (1H, m), 2.55 (3H, s), 2.25 (3H, s), 1.68–1.5 (2H, m), 1.25 (3H, d, J=7 Hz), 0.85 (3H, t, J=7 Hz)

IR (KBr) cm⁻¹:3255, 1647, 1078, 791

Elemental analysis (%): Calc'd for $C_{17}H_{21}NO_2$: C, 75.25; H, 7.80; N, 5.16. Found: C, 75.19; H, 7.68; N, 5.14

EXAMPLE 26

2,5-Dimethylfuran-3-carboxy(3-pentylanilide)

Yield:18.3% m.p.:97.0–97.5° C.

$^1$H NMR (CDCl$_3$) δ ppm: 7.45 (1H, m), 7.35 (1H, m), 7.28 (1H, b), 7.25 (1H, t, J=8 Hz), 6.95 (1H, d, J=8 Hz), 6.1 (1H, s), 2.65–2.5 (2H, m), 2.55 (3H, s), 2.25 (3H, s), 1.7–1.5 (2H, m), 1.4–1.2 (4H, m), 0.88 (3H, t, J=7 Hz)

IR (KBr) cm$^{-1}$:3304, 1644, 1077, 710

Elemental analysis (%): Calc'd for C$_{18}$H$_{23}$NO$_2$: C, 75.76; H, 8.12; N, 4.91. Found: C, 75.77; H, 8.18; N, 5.06

EXAMPLE 27

2,5-Dimethylfuran-3-carboxy-(3-cyclohexylanilide)

Yield:52.7% m.p.:113.0–114.5° C.

$^1$H NMR (CDCl$_3$) δ ppm: 7.48 (1H, m), 7.35 (1H, m), 7.28 (1H, b), 7.25 (1H, t, J=8 Hz), 6.98 (1H, d, J=8 Hz), 6.1 (1H, s), 2.55 (3H, s), 2.55–2.45 (1H, m), 2.25 (3H, s), 1,95–1.68 (5H, m), 1.55–1.15 (5H, m)

IR (KBr) cm$^{-1}$:3324, 1646, 1230, 1074, 791

Elemental analysis (%): Calc'd for C$_{19}$H$_{23}$NO$_2$: C, 76.74; H, 7.80; N, 4.71. Found: C, 76.62; H, 7.78; N, 4.67

EXAMPLE 28

2,5-Dimethylfuran-3-carboxy(3-cyclopentylanilide)

Yield:35.9% m.p.:92.0–93.0° C.

$^1$H NMR (CDCl$_3$) δ ppm: 7.45 (1H, m), 7.35 (1H, m), 7.25 (1H, b), 7.22 (1H, t, J=8 Hz), 7.00 (1H, d, J=8 Hz), 6.1 (1H, s), 3.08–2.9 (1H, m), 2.55 (3H, s), 2.25 (3H, s), 2.15–1.95 (2H, m), 1.9–1.5 (6H, m)

IR (KBr) cm$^{-1}$:3322, 1647, 1232, 1076, 700

Elemental analysis (%): Calc'd for C$_{18}$H$_{21}$NO$_2$: C, 76.30; H, 7.47; N, 4.94. Found: C, 76.21; H, 7.56; N, 4.93

EXAMPLE 29

2,5-Dimethylfuran-3-carboxy(3-benzylanilide)

Yield:59.8% m.p.:123.0–125.0° C.

$^1$H NMR (CDCl$_3$) δ ppm: 7.45 (1H, m), 7.38 (1H, m), 7.35–7.15 (7H, m), 6.95 (1H, d, J=8 Hz), 3.98 (2H, s), 2.55 (3H, s), 2.25 (3H, s)

IR (KBr) cm$^{-1}$:3314, 1640, 1078, 777, 701

Elemental analysis (%): Calc'd for C$_{21}$H$_{19}$NO$_2$: C, 78.66; H, 6.27; N, 4.59. Found: C, 77.76; H, 6.28; N, 4.55

REFERENTIAL EXAMPLE 1

Ethyl 2,5-Dimethylfuran-3-carboxylate

To a suspension of 2.4 g of sodium hydride (60% dispersion in mineral oil) in 10 ml of N,N-dimethylformamide (hereinafter, abbreviated as DMF) a solution of 6.5 ml of ethyl acetoacetate in 5 ml of DMF was added dropwise with stirring under ice-cooling, and 5.97 ml of chloroacetone were added dropwise thereto with stirring under ice-cooling. After stirring at room temperature for 3 hours, the reaction mixture was poured into water and the aqueous mixture was extracted with ethyl acetate. The extract was washed with a saturated aqueous solution of sodium chloride and dried over anhydrous sodium sulfate. After distilling off the solvent under reduced pressure, the residue was distilled in vacuo to give 8.01 g of ethyl α-acetonitrile-acetoacetate having b.p. 105° C./2 mmHg in a 86% yield.

To a solution of the ester thus obtained in 20 ml of ethanol were added 2 g of p-toluenesulfonic acid, and the resulting mixture was heated under reflux for 2 hours. The reaction mixture was allowed to cool to room temperature and the solvent was distilled off under reduced pressure. The residue was dissolved in ethyl acetate and the solution was washed with a saturated aqueous solution of sodium chloride followed by drying over anhydrous magnesium sulfate. After distilling off the solvent under reduced pressure, the residue was purified by column chromatography through silica gel using a 10:1 mixture of n-hexane and ethyl acetate as an eluent to give 5.14 g of ethyl 2,5-dimethylfuran-3-carboxylate in a 71% yield.

REFERENTIAL EXAMPLE 2

2,5-Dimethylfuran-3-carboxylic acid

A mixture of 3.2 g of ethyl 2,5-dimethylfuran-3-carboxylate, 35 ml of ethanol and 20 ml of 2 N sodium hydroxide was stirred at room temperature for 1.5 hours followed by heating under reflux for an hour. After the reaction mixture was allowed to cool to room temperature, it was concentrated under reduced pressure. The residue was dissolved in water and acidified with diluted sulfuric acid. Precipitated crystals were collected by filtration, washed with water and dried to give 2.27 g of 2,5-dimethylfuran-3-carboxylic acid in a 85% yield.

The compound having the general formula (I) mentioned above and the composition containing the compound (I) as the active ingredient, with which the present invention are concerned, can be employed by mixing with carriers or, if necessary, with any other additives, followed by the preparation of formulations usually employed such as oil solution, emulsifiable concentrate, solubilizer, paste, wettable powder, flowable, dry flowable, spray and paint, and then the formulation can be used according to any known method for wood preservative treatment. As the additives which are employed suitably to improve the property of the formulation and to strengthen the wood preserving effect, there may be mentioned cationic, anionic and non-ionic surfactants, various high polymer compounds such as methylcellulose and vinyl acetate resin and water-repellents such as silicon oil and paraffin. It is needless to say that combined use may be possible with other wood preservatives, fungicides and bateriocides including organic iodine compounds such as Sanplas, IF-1000 and Troysan, azole compounds such as Propiconazole and Tebuconazole, Thiabendazole, Dichlofluanid and quaternary ammonium salt compounds; with insecticides including pyrethroids such as Permethrin, Etofenprox, Cypermethrin, Silaneophen, Tralomethrin, organic phosphor compounds such as Chloropyrifos, Phoxim and Propetamphos, with Imidacroprid; and with potentiators such as bi-(2,3,3,3-tetrachloropropyl) ether. An increased effect can be expected by combined use in this manner. In a real case of application, through the content of the compound of the present invention can be changed within a wide range depending on the formulation or on the object, it may usually be suitable to use from 0.1 to 95 weight percent, preferably from 0.2 to 60 weight percent. These formulations are employable in usual methods for wood treatment: for example, coating, dispersal, dipping treatment, mixing, impreganation, or mixing treatment with an adhesive.

Several formulation examples of the compound of the present invention will be shown below, in which it is needless to say that the combination ratio and the kind of additives can be changed widely (in the descriptions below, part means weight part in all cases).

FORMULATION EXAMPLES OF THE WOOD PRESERVATIVES

FORMULATION EXAMPLE 1

Emulsifiable Concentrate

Twenty parts of the Compound of Example 20 were dissolved in 70 parts of xylene, and then 10 parts of polyoxyethylene nonyl phenyl ether were added and mixed enough to obtain the emulsifiable concentrate.

Thus obtained emulsifiable concentrate is diluted with a suitable amount of water at use, and can be applied to a wood material to be treated by coating, dipping or spraying, and in addition, employable by mixing with adhesives which are used for plywood, particle board and hardboard.

FORMULATION EXAMPLE 2

Oil Solution

Two parts of the Compound of Example 21 were added with 98 parts of kerosene oil to obtain the oil solution.

Thus obtained oil solution can be applied to a wood material to be treated by spraying, coating, dipping or impregantion.

FORMULATION EXAMPLE 3

Coating Formulation

Ten parts of the Compound of Example 20, 20 parts of Barite dust, 10 parts of vinyl resin, 25 parts of pine resin and 35 parts of xylene were mixed homogeneously to obtain the coating formulation.

FORMULATION EXAMPLE 4

Wettable Powder

Forty parts of the Compound of Example 22, 56 parts of clay, 3 parts of sodium lauryl alcohol sulfonate and 1 part of polyvinyl, alcohol were mixed homogeneously in a mixer, and pulverized by use of a hammer-mill to obtain the wettable powder.

TEST EXAMPLES OF WOOD PRESERVATION

The effectiveness of the wood preservative of the present invention will be explained concretely by the following examples.

(1) According to the test method for wood preservation described in the Japan Industrial Standards [JIS A-9201 (1991)], each of the test compounds was dissolved to a defined concentration in methanol. The solution was impregnated under a reduced pressure into a Sugi (Japanese cedar) sapwood (2×2×1) cm and then air-dried. Weathering test was repeated 10 times in which one cycle of the treatment was stirring in water for 8 hours, and then heating for 16 hours at 60° C. The test material was placed on the flora of *Serpula lacrymans* which had been previously grown on a quartz sand medium (malt extract 2%, glucose 1%, peptone 0.3% and yeast 0.2%), and forcedly decayed at 20° C. for 12 weeks. From the difference between the dry weight of the test material before the test and that after test, the degree of decrease in weight was obtained. Table 2 shows the results. The test was carried out by use of 9 samples for each condition, and the values shown in Table 2 are the mean values calculated from 9 samples.

TABLE 2

| Sample drugs decrease | Impregnant concentration (%) | Mean weight by decay (%) |
| --- | --- | --- |
| Example 20 | 0.01 | 0 |
|  | 0.005 | 0.1 |
| Example 21 | 0.01 | 0 |
|  | 0.005 | 0 |
| Control compound 1 | 0.01 | 9.7 |
|  | 0.005 | 18.6 |
| Without treatment |  | 18.4 |

Control compound 1: 4-Chlorophenyl-3-iodopropargylformal Product of Nagase Co., Ltd.: IF-1000

From the data shown above, the compound having the general formula (I) prevented decay of the wood samples due to wood-rotting fungi to a significant extent.

(2) Each of 0.1 w/v % methanol solutions of the compound of the present invention and the control drug was impregnated into the test material [a Sugi (Japanese cedar) sapwood, 2×2×0.5 cm] under a reduced pressure and then air-dried. Weathering test was repeated twice in which one cycle of the treatment was washing (about 2 liter per minute supply) with water for 5 hours, and then heating for 19 hours at 60° C. After dry air sterilization, the test samples were prepared.

The test materials were placed on the flora of *Coriolus versicolor* which is a lignin-decomposing fungus, and of *Tryomyces palustris* which is a cellulose-decomposing fungus, and both of which are designated fungal species for assay of wood preservating effect. Both fungi had been previously grown on an agar medium (malt extract 2%, glucose 1% and peptone 0.5%). After the wood samples were forcedly deteriorated at 26° C. for 3 weeks, the effectiveness was determined from the degree of hyphal growth on the test material and the presence or absence of lowered maximum crushing strength. Table 3 shows the result.

The wood preventive efficacy was judged by the following criteria.

+: No hyphal growth was observed on the test material, and no difference was found in the maximum crushing strength from the healthy wood sample.

±: A little hyphal growth was observed on the test material, or a little decrease was found in the maximum crushing strength.

−: Hyphal growth was observed on the test material, or clear decrease was found in the maximum crushing strength.

TABLE 3

| Test drug | Coriolus versicolor | Tyromyces palustris |
| --- | --- | --- |
| Example 1 | ± | − |
| Example 2 | − | − |
| Example 3 | − | − |
| Example 4 | − | − |
| Example 5 | − | − |
| Example 6 | + | + |
| Example 7 | + | − |
| Example 8 | ± | − |

TABLE 3-continued

| Test drug | Coriolus versicolor | Tyromyces palustris |
|---|---|---|
| Example 9 | − | − |
| Example 10 | + | − |
| Example 11 | + | ± |
| Example 12 | ± | ± |
| Example 13 | + | + |
| Example 14 | + | + |
| Example 15 | + | − |
| Example 20 | + | + |
| Example 21 | + | + |
| Example 23 | + | + |
| Example 24 | + | + |
| Example 25 | + | + |
| Example 26 | + | + |
| Control compound 2 | + | + |
| Without treatment | − | − |

Control compound 2: 3-Bromo-2,3-diiodo-2-propenylethylcarbonate Product of Sankyo Co., Ltd.: Sanplas When the composition of the present invention is desired to be employed, the combination ratio may be suitably selected depending on the kind of wood and the kind of wood material to be treated with the wood preservative, or the means for treatment (for example, coating, dipping, dispersal, impregnation, mixing and mixing with an adhesive). Usually, the combination ratio of dimethylfurancarboxyanilide and any other wood preservative may be from 240:1 to 1:35, preferably from 30:1 to 1:10, and more preferably from 5:1 to 1:5.

The content of the composition of the present invention may be changed within a wide range depending on the formulation. In general, the content may be from 0.1 to 95%, preferably from 0.2 to 60%, in the formulation.

Several formulation examples of the compound of the present invention will be shown below, in which it is needless to say that the combination ratio and the kind of additives can be changed widely.

FORMULATION EXAMPLES OF THE WOOD PRESERVATIVE COMPOSITION

FORMULATION EXAMPLE 1

Emulsifiable Concentrate

Ten parts of the Compound of Example 20 were dissolved in 30 parts of Sanplas and 50 parts of xylene, 10 parts of polyoxyethylene nonyl phenyl ether were then added and mixed enough to obtain the emulsifiable concentrate.

Thus obtained emulsifiable concentrate is diluted with a suitable amount of water at the time of use, and can be applied to a wood material to be treated by coating, dipping or spraying, and in addition, employable by mixing with adhesives which are used for plywood, particle board and hardboard.

FORMULATION EXAMPLE 2

Oil Solution

Two parts of the compound of Example 21 and 1 part of troysan were dissolved in 96 parts of kerosene oil to obtain the oil solution.

FORMULATION EXAMPLE 3

Wettable Powder

Fifteen parts of the compound of Example 22, 25 parts of IF-1000, 56 parts of clay, 3 parts of sodium lauryl alcohol sulfonate and 1 part of polyvinyl alcohol were mixed homogeneously in a mixer, and pulverized by use of a hammer-mill to obtain the wettable powder.

The effect of the wood preservative composition of the present invention will be explained concretely by the following examples.

TEST EXAMPLES OF WOOD PRESERVATIVE COMPOSITIONS

Assay of minimum inhibitory concentration by the agar dilution method.

According to the agar dilution method, on sterilized media (potato dextrose agar medium; potato extract powder 0.4%, glucose 2%, agar 1.5%) prepared to contain certain concentrations of a test sample, flora (about 4 mm in diameter) of wood rotting fungi, *Coriolus versicolor* and *Tyromyces palustris*, which has been cultured previously on the same kind of medium, were inoculated. After culture at 25° C. for 5 days, hyphal growth was observed to determine the minimum inhibitory concentration.

Whether there is any potentiation or not has been described in Applied Microbiology 9, 538–541 (1961) by F. C. Kull et al. The assay was carried out according to the method usually employed.

Figure 1B:
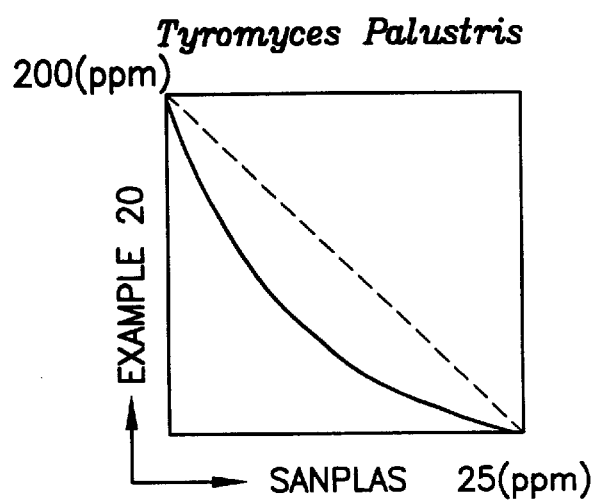
Figure 1C:
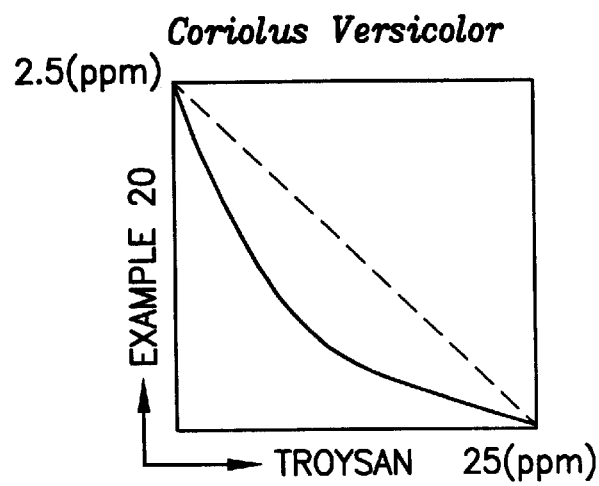
Figure 1D:
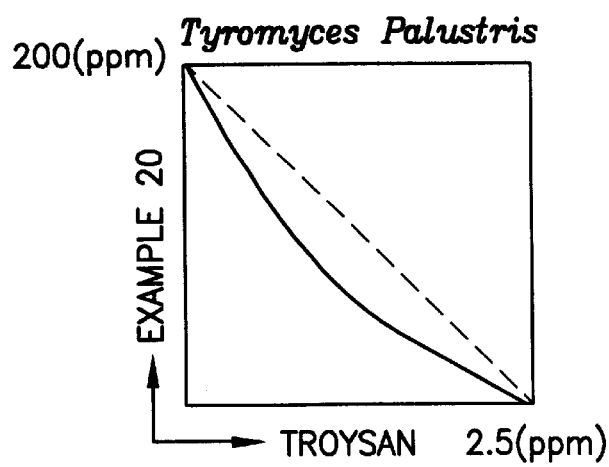
Figure 1E:
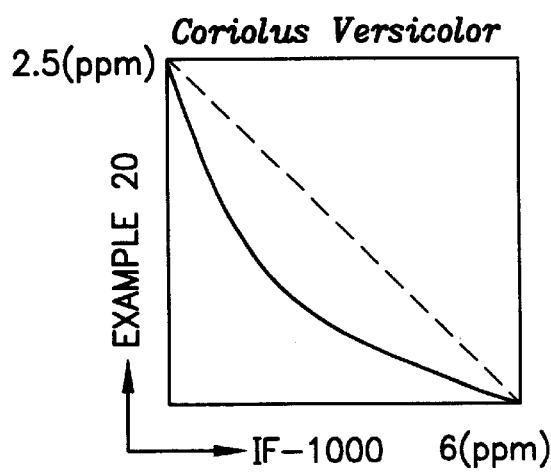
Figure 1F:
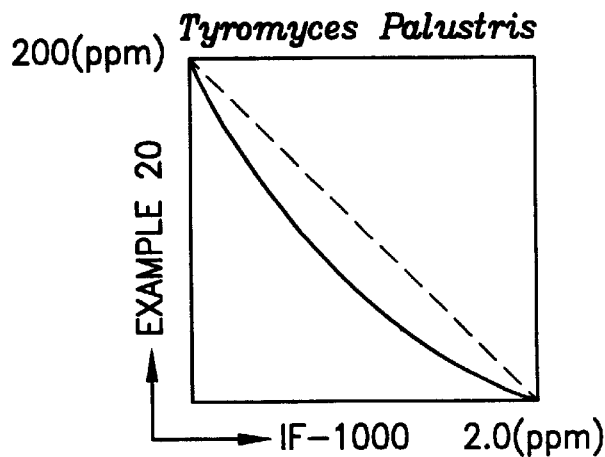

Table 4 and FIGS. 1A to 1F show the results obtained by combination of Example 20 with each of Sanplas, Troysan and IF-1000.

TABLE 4-1

| Test fungus | MIC (ppm) of Example 20 combined with several other active agents | | | |
|---|---|---|---|---|
| | Example 20 | A | Example 20 + A | (Combined ratio) Example 20:A |
| Coriolus Versicolor | 2.5 | 15 | 1.30 + 3.0 | (1:2.3) |
| | | | 0.8 + 5.0 | (1:6.3) |
| | | | 0.4 + 9.0 | (1:22.5) |
| Tyromyces Palustris | 200 | 25 | 110.0 + 5.0 | (22:1) |
| | | | 70.0 + 9.0 | (7.8:1) |
| | | | 40.0 + 14.0 | (2.9:1) |

A: Sanplas

TABLE 4-2

| Test fungus | MIC (ppm) of Example 20 combined with several other active agents | | | |
|---|---|---|---|---|
| | Example 20 | B | Example 20 + B | (Combined ratio) Example 20:B |
| Coriolus Versicolor | 2.5 | 25 | 1.25 + 5.0 | (1:4) |
| | | | 0.8 + 7.5 | (1:9.4) |
| | | | 0.4 + 12.5 | (1:31.3) |
| Tyromyces Palustris | 200 | 2.5 | 120.0 + 0.6 | (200:1) |
| | | | 80.0 + 1.0 | (80:1) |
| | | | 40.0 + 1.5 | (26.7:1) |

B: Troysan

TABLE 4-3

| Test fungus | MIC (ppm) of Example 20 combined with several other active agents | | | |
|---|---|---|---|---|
| | Example 20 | C | Example 20 + C | (Combined ratio) Example 20:C |
| Coriolus Versicolor | 2.5 | 6 | 1.25 + 1.2 | (1.0:1) |
| | | | 0.8 + 1.8 | (1:2.3) |
| | | | 0.5 + 3.0 | (1:6) |

TABLE 4-3-continued

MIC (ppm) of Example 20 combined with several other active agents

| Test fungus | Example 20 | C | Example 20 + C | (Combined ratio) Example 20:C |
|---|---|---|---|---|
| Tyromyces Palustris | 200 | 2 | 120.0 + 0.5 | (240:1) |
| | | | 80.0 + 0.8 | (100:1) |
| | | | 40.0 + 1.2 | (33:1) |

C: IF-1000

Figure 2A:
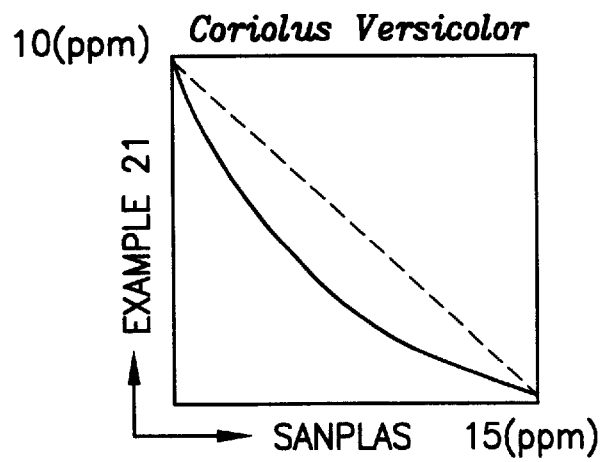
FIGS. 2A to 2F show the minimum inhibitory concentrations (ppm) of Compound of Example 21 in combination with various wood preservatives.
Figure 2B:
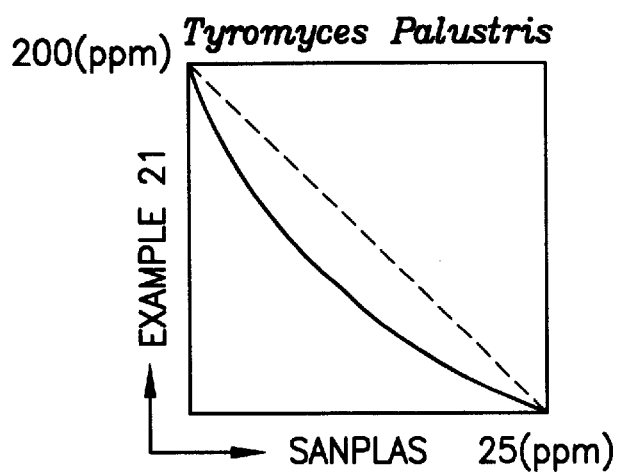
Figure 2C:
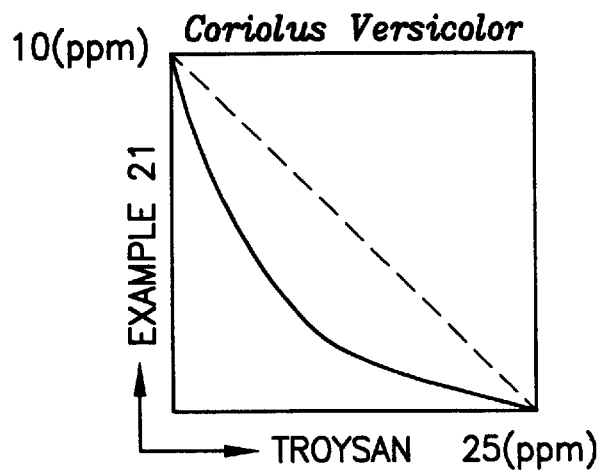
Figure 2D:
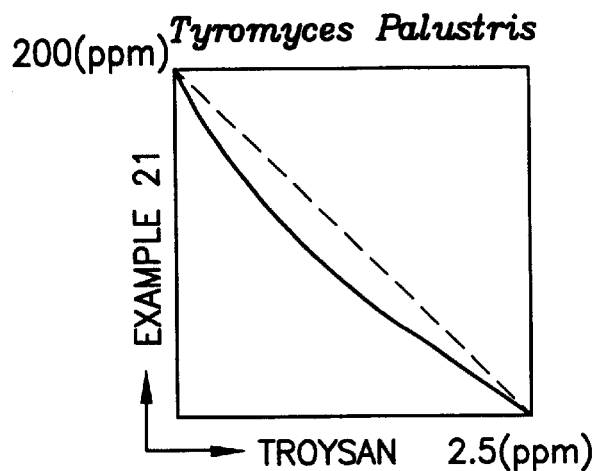
Figure 2E:
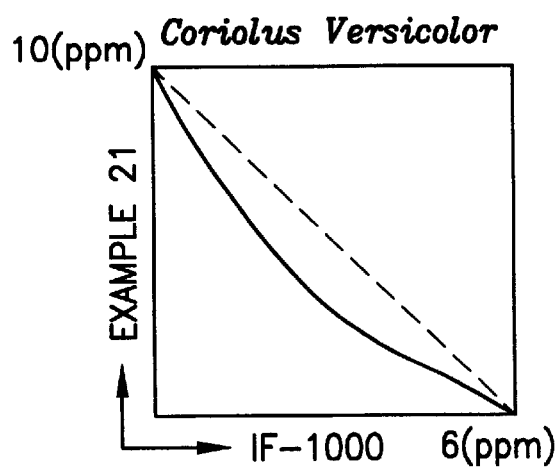
Figure 2F:
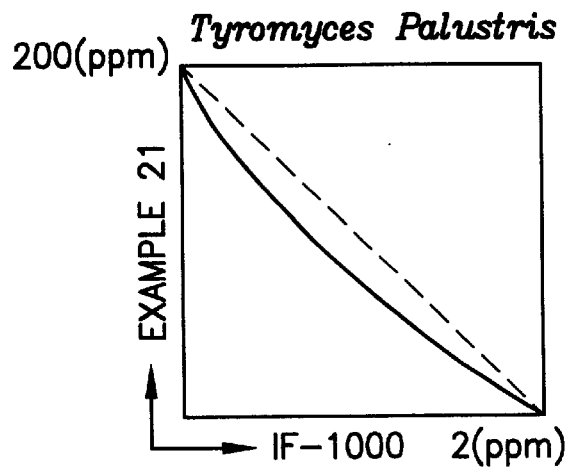

Then, the same test as above was carried out for Example 21. Table 5 and FIGS. 2A to 2F show the result.

TABLE 5-1

MIC (ppm) of Example 21 combined with several other active agents

| Test fungus | Example 21 | A | Example 21 + A | (Combined ratio) Example 21:A |
|---|---|---|---|---|
| Coriolus Versicolor | 10.0 | 15 | 6.0 + 3.0 | (2:1) |
| | | | 3.5 + 5.0 | (1:1.4) |
| | | | 2.0 + 8.0 | (1:4) |
| Tyromyces Palustris | 200 | 25 | 120.0 + 5.0 | (24:1) |
| | | | 75.0 + 9.0 | (8.3:1) |
| | | | 40.0 + 15.0 | (2.7:1) |

A: Sanplas

TABLE 5-2

MIC (ppm) of Example 21 combined with several other active agents

| Test fungus | Example 21 | B | Example 21 + B | (Combined ratio) Example 21:B |
|---|---|---|---|---|
| Coriolus Versicolor | 10.0 | 25 | 5.5 + 5.0 | (1.1:1) |
| | | | 3.0 + 8.0 | (1:2.7) |
| | | | 1.5 + 12.5 | (1:8.3) |
| Tyromyces Palustris | 200 | 2.5 | 120.0 + 0.7 | (171.4:1) |
| | | | 90.0 + 1.0 | (90:1) |
| | | | 40.0 + 1.75 | (22.9:1) |

B: Troysan

TABLE 5-3

MIC (ppm) of Example 21 combined with several other active agents

| Test fungus | Example 21 | C | Example 21 + C | (Combined ratio) Example 21:C |
|---|---|---|---|---|
| Coriolus Versicolor | 10.0 | 6 | 6.0 + 1.6 | (3.6:1) |
| | | | 4.0 + 2.4 | (1.7:1) |
| | | | 2.0 + 3.6 | (1:1.8) |
| Tyromyces Palustris | 200 | 2 | 120.0 + 0.5 | (240:1) |
| | | | 90.0 + 1.0 | (90:1) |
| | | | 40.0 + 1.4 | (28.6:1) |

C: IF-1000

Each of the minimum inhibitory concentration curves shown in FIGS. 1A to 1F and FIGS. 2A to 2F lies under the diagonal line shown by broken line.

This data exhibits that the furancarboxyanilide derivative potentiates the effect of each of Sanplas, Troysan and IF-1000 by combination.

We claim:

1. A dimethylfurancarboxyanilide compound of the formula (I):

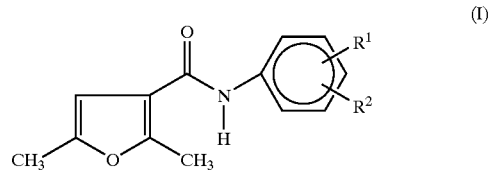

wherein $R^1$ or $R^2$ or both $R^1$ and $R^2$ are a benzyl group selected from the group consisting of benzyl, 2-methylbenzyl, 2,4-dimethylbenzyl, 2-chlorobenzyl, 4-methoxybenzyl and 4-ethoxybenzyl.

2. The dimethylfurancarboxyanilide compound of claim 1, wherein the compound is 2,5-dimethylfuran-3-carbonyl (3-benzylanilide).

3. The dimethylfurancarboxyanilide compound of claim 1, wherein the compound is 2,5-dimethylfuran-3-carboxy[3-(4-methoxybenzyl)anilide].

4. A dimethylfurancarboxyanilide compound which is 2,5-dimethylfuran-3-carboxy(3-isopropylanilide).

5. A dimethylfurancarboxyanilide compound which is 2,5-dimethylfuran-3-carboxy(3-isopropyloxymethylanilide).

6. A dimethylfurancarboxyanilide compound which is 2,5-dimethylfuran-3-carboxy[3-(2-methoxycarbonylvinyl)anilide].

* * * * *